United States Patent
Zilberman et al.

(10) Patent No.: US 8,301,266 B1
(45) Date of Patent: Oct. 30, 2012

(54) STRUCTURE FOR PLACEMENT OF AN IMPLANTABLE DEVICE

(75) Inventors: Yitzhak Zilberman, Santa Clarita, CA (US); Ross Davis, Melbourne Beach, FL (US); Lee J. Mandell, West Hills, CA (US); Joseph H. Schulman, Santa Clarita, CA (US)

(73) Assignee: Alfred E. Mann Foundation For Scientific Research, Santa Clarita, CA (US)

( * ) Notice: Subject to any disclaimer, the term of this patent is extended or adjusted under 35 U.S.C. 154(b) by 351 days.

(21) Appl. No.: 12/233,482

(22) Filed: Sep. 18, 2008

Related U.S. Application Data (62) Division of application No. 10/718,836, filed on Nov. 21, 2003, now Pat. No. 7,450,998.

(51) Int. Cl.
*A61N 1/05* (2006.01)

(52) U.S. Cl. .................... 607/118; 607/117

(58) Field of Classification Search ........... 607/117–118
See application file for complete search history.

(56) References Cited

U.S. PATENT DOCUMENTS

| | | | |
|---|---|---|---|
| 4,573,481 A * | 3/1986 | Bullara | 607/118 |
| 5,358,514 A * | 10/1994 | Schulman et al. | 607/61 |
| 6,600,956 B2 * | 7/2003 | Maschino et al. | 607/118 |
| 7,054,692 B1 * | 5/2006 | Whitehurst et al. | 607/149 |

* cited by examiner

*Primary Examiner* — Niketa Patel
*Assistant Examiner* — Joseph Stoklosa
(74) *Attorney, Agent, or Firm* — Gary D. Schnittgrund (57) ABSTRACT

A device configured for implantation beneath a patient's skin for the purpose of tissue, e.g., nerve or muscle, stimulation and/or parameter monitoring and/or data communication. Devices in accordance with the invention are comprised of a sealed housing, typically having an axial dimension of less than 60 mm and a lateral dimension of less than 6 mm, containing a power source for powering electronic circuitry within. A placement structure is shown for facilitating placement of the implantable device proximate to neural/muscular tissue.

14 Claims, 9 Drawing Sheets

STRUCTURE FOR PLACEMENT OF AN IMPLANTABLE DEVICE

CROSS-REFERENCE TO RELATED APPLICATION

This application is a divisional of U.S. patent application Ser. No. 10/718,836, filed Nov. 21, 2003; now U.S. Pat. No. 7,450,998, issued Nov. 11, 2008, which is incorporated in its entirety by reference.

SUMMARY OF THE INVENTION

In a preferred embodiment of the present invention, a placement structure is shown for facilitating placement of an implantable device having at least two electrodes proximate to neural/muscular tissue, wherein the placement structure comprises (1) a holder having a hollow cavity formed within for holding and retaining the implantable device within; (2) at least one set of elastic wings for capturing neural/muscular tissue; and wherein the placement structure is primarily formed from a biocompatible plastic.

The novel features of the invention are set forth with particularity in the appended claims. The invention will be best understood from the following description when read in conjunction with the accompanying drawings.

BRIEF DESCRIPTION OF THE DRAWINGS

FIG. 3 is a perspective view of an exemplary placement structure of the present invention which is formed for holding one of the implantable devices in close proximity to a nerve, muscle tissue, or the like.

DETAILED DESCRIPTION OF THE PREFERRED EMBODIMENTS

Figure 1:
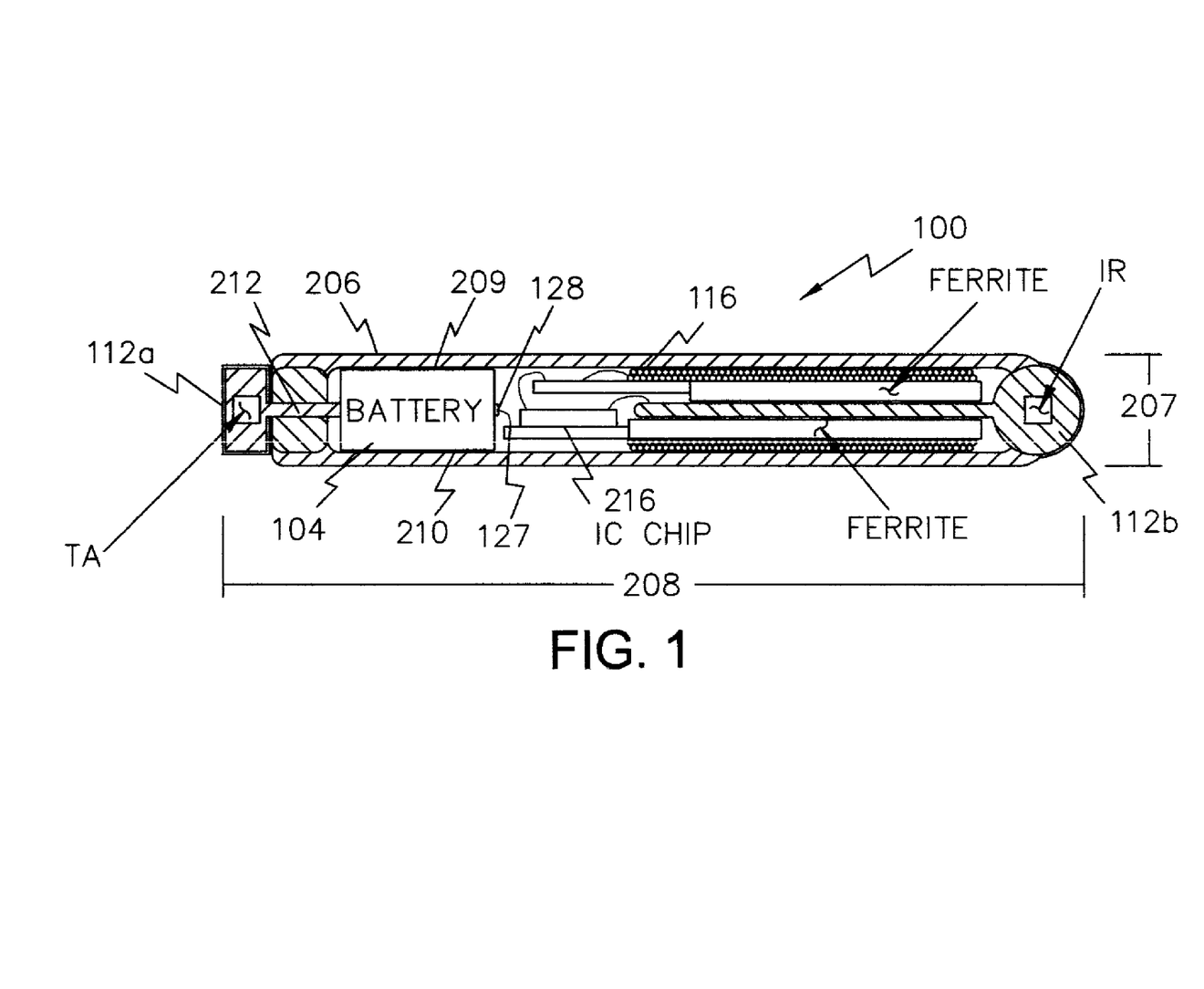
FIG. 1 shows a side view of a battery-powered implanted device, e.g., a microstimulator, made in accordance with the present invention.

FIG. 1 shows a side view of a microstimulator 100 which includes battery 104 for powering the circuitry within. The battery 104 conveniently fits within a sealed elongate housing 206 (preferably hermetically sealed) which encases the microstimulator 100. In a preferred device 100, the axial dimension 208 is less than 60 mm and the lateral dimension 207 is less than 6 mm.

For the embodiment shown in FIG. 1, the battery 104 is preferably housed within its own battery case 209, with the battery terminals comprising an integral part of its case 209 (much like a conventional AA battery). Thus, the sides and left end of the battery 104 (as oriented in FIG. 1) may comprise one battery terminal 210, e.g., the negative battery terminal, and the right end of the battery 104 may comprise the other battery terminal, e.g., the positive battery terminal used as the output terminal 128. Advantageously, because such a battery case 209 is conductive, it may serve as an electrical conductor for connecting an appropriate circuit node for the circuitry within the microstimulator 100 from one side of the battery to the other. More particularly, for the configuration shown in FIG. 1, the battery terminal 210 may serve as a ground point or node for all of the circuitry housed within the device housing 206. Hence, stem 212 from the electrode 112a on the left end of the microstimulator 100, which from an electrical circuit point of view is simply connected to circuit ground, may simply contact the left end of the battery 104. Then, this same circuit ground connection is made available near or on the rim of the battery 104 on its right side, near one or more IC chips 216 (preferably implementing the device's power consuming circuitry, e.g., the controller 106 and stimulation circuitry 110) on the right side of battery 104 within the right end of the housing 206. By using the conductive case 209 of the battery 104 in this manner, there is no need to try to pass or fit a separate wire or other conductor around the battery 104 to electrically connect the circuitry on the right of the device 100 with the electrode 112a on the left side of the device 100.

The electrodes 112a and 112b for the microstimulator 100 shown in FIG. 1 are made from iridium (electrode 112b) and tantalum (electrode 112a), and such materials inherently provide a substantial capacitance between them, thereby preventing DC current flow. See, e.g., col. 11, lines 26-33, of U.S. Pat. No. 5,324,316.

Figure 2:
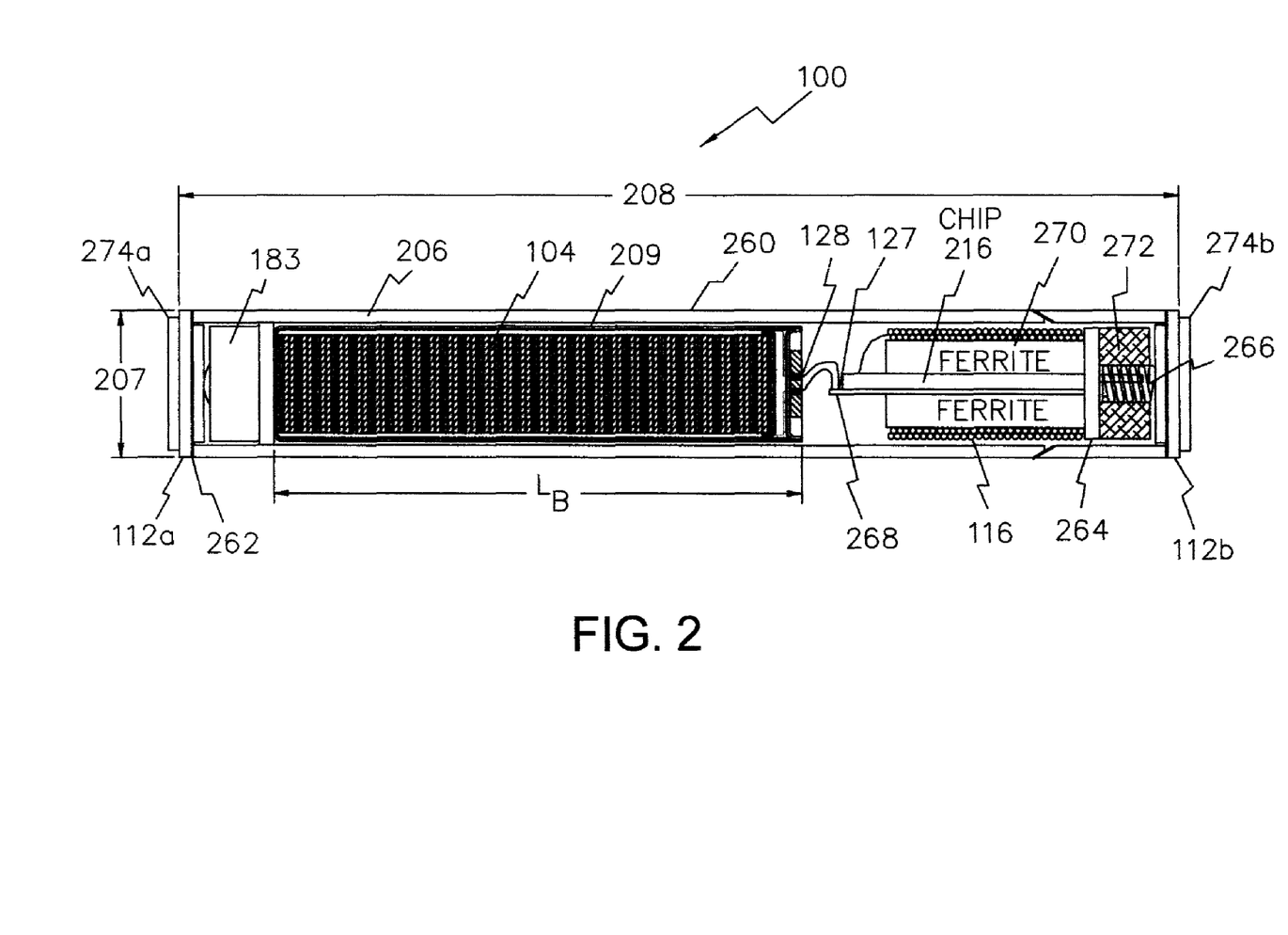
FIG. 2 shows a side cutaway views of an implantable ceramic tube suitable for housing the system control unit and/or microstimulators and/or microsensors and/or microtransponders.

FIG. 2 shows a side cutaway view of the sealed housing 206, the battery 104 and the circuitry (implemented on one or more IC chips 216 to implement electronic portions of the SCU 302) contained within. In this presently preferred construction, the housing 206 is comprised of an insulating ceramic tube 260 brazed onto a first end cap forming electrode 112a via a braze 262. At the other end of the ceramic tube 260 is a metal ring 264 that is also brazed onto the ceramic tube 260. The circuitry within, i.e., a capacitor 183 (used when in a microstimulator mode), battery 104, IC chips 216, and a spring 266 is attached to an opposing second end cap forming electrode 112b. A drop of conductive epoxy is used to glue the capacitor 183 to the end cap 112a and is held in position by spring 266 as the glue takes hold. Preferably, the IC chips 216 are mounted on a circuit board 268 over which half circular longitudinal ferrite plates 270 are attached. The coil 116 is wrapped around the ferrite plates 270 and attached to IC chips 216. A getter 272, mounted surrounding the spring 266, is preferably used to increase the hermeticity of the SCU 302 by absorbing water introduced therein. An exemplary getter 272 absorbs 70 times its volume in water. While holding the circuitry and the end cap 112b together, one can laser weld the end cap 112b to the ring 264. Additionally, a platinum, iridium, or platinum-iridium disk or plate 274 is preferably welded to the end caps of the SCU 302 to minimize the impedance of the connection to the body tissue.

FIGS. 3-13 are directed to a placement structure 500 that is useful for placing and retaining one of the aforementioned implantable devices 100 in close proximity to a nerve, muscle tissue, or the like, i.e., neural/muscular tissue. For the purposes of this application neural/muscular tissue is understood to signify tissue that passes or responds to neural signals which includes nerve fibers or muscle tissue or any combination thereof. This structure 500 may present additional benefits, e.g., higher sensing sensitivity or lower stimulation power and thus longer battery life between chargings. The placement structure 500 is preferably comprised of two main portions: (1) a holder 502 for holding and retaining the implantable device 100 within and (2) one or more sets (e.g., pairs) of wings 504 for capturing neural/muscular tissue. Preferably, the placement structure 500 is primarily formed from of a biocompatible plastic silicone elastomer, e.g., SILASTIC®, a registered trademark of Dow Corning, that is elastic and is also an electrical insulator. In an exemplary embodiment, the holder 502 is essentially semi-circular in cross section and has a hollow cavity 506 having end plates 508 and 510 that essentially conforms to the size and shape of implantable device 100 such that the implantable device 100 may be snapped into the cavity 506 and is held by the elasticity of the holder 502 (see FIGS. 3 and 4) which show the insertion of the implantable device 100 into the cavity 506 of the holder 502 of the placement structure 500. It should be noted that while the exemplary capture device 500 is shown for holding an implantable device 100 having a circular cross section, it should be readily apparent to one of ordinary skill in the art that this exemplary structure is readily alterable to accommodate devices having non-circular cross sections as well.

Figures 5, 6, 7:
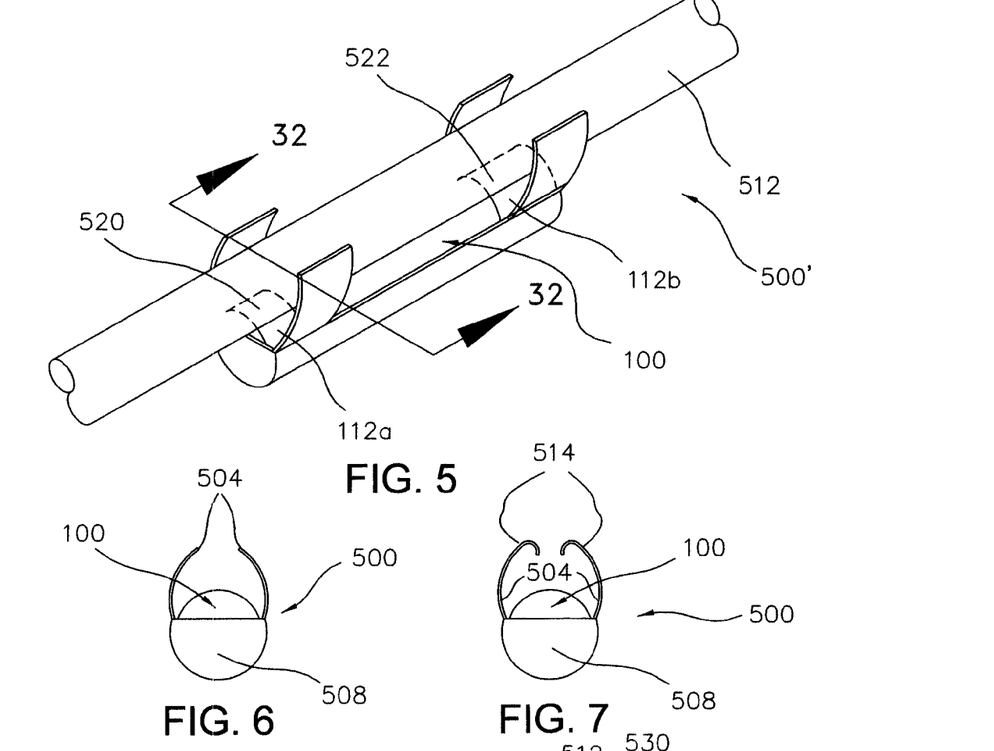
FIG. 5 is a perspective view of the placement structure of FIGS. 3 and 4 showing its wings capturing neural/muscular tissue.
FIG. 6 is an end view of the placement structure of FIGS. 3 and 4.
FIG. 7 is an end view of the placement structure of FIGS. 3 and 4 having hooks at the ends of its wings for providing additional means for retaining the placement structure in close proximity to the neural/muscular tissue.
Figure 10:
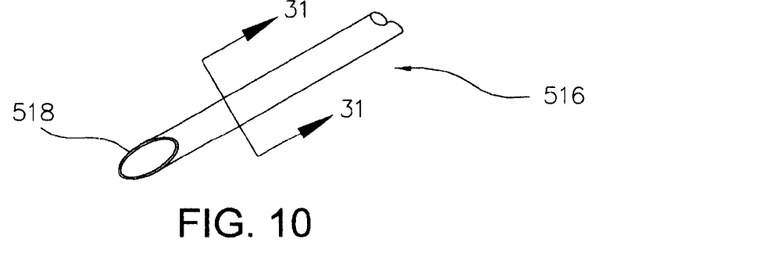
FIG. 10 is a cross sectional view of that shown in FIG. 5 along the line 32-32 showing the wings of the placement structure holding neural/muscular tissue and the resulting stimulation/sensing vectors.
Figure 11:
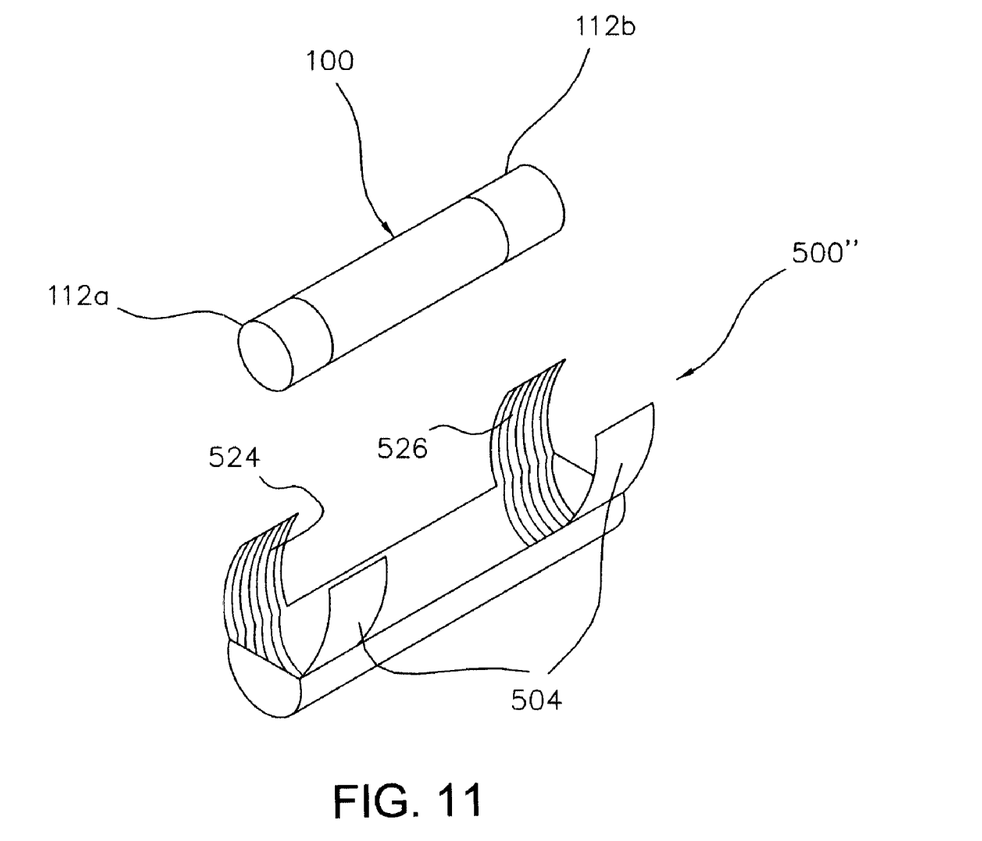
FIG. 11 is an alternative embodiment of the placement structure of FIG. 3 wherein inner portions of the wings and the cavity include conductive layers (preferably a plurality of conductive paths) to provide additional electrical coupling between the electrodes of the implantable device axially along the neural/muscular tissue.
Figure 12:
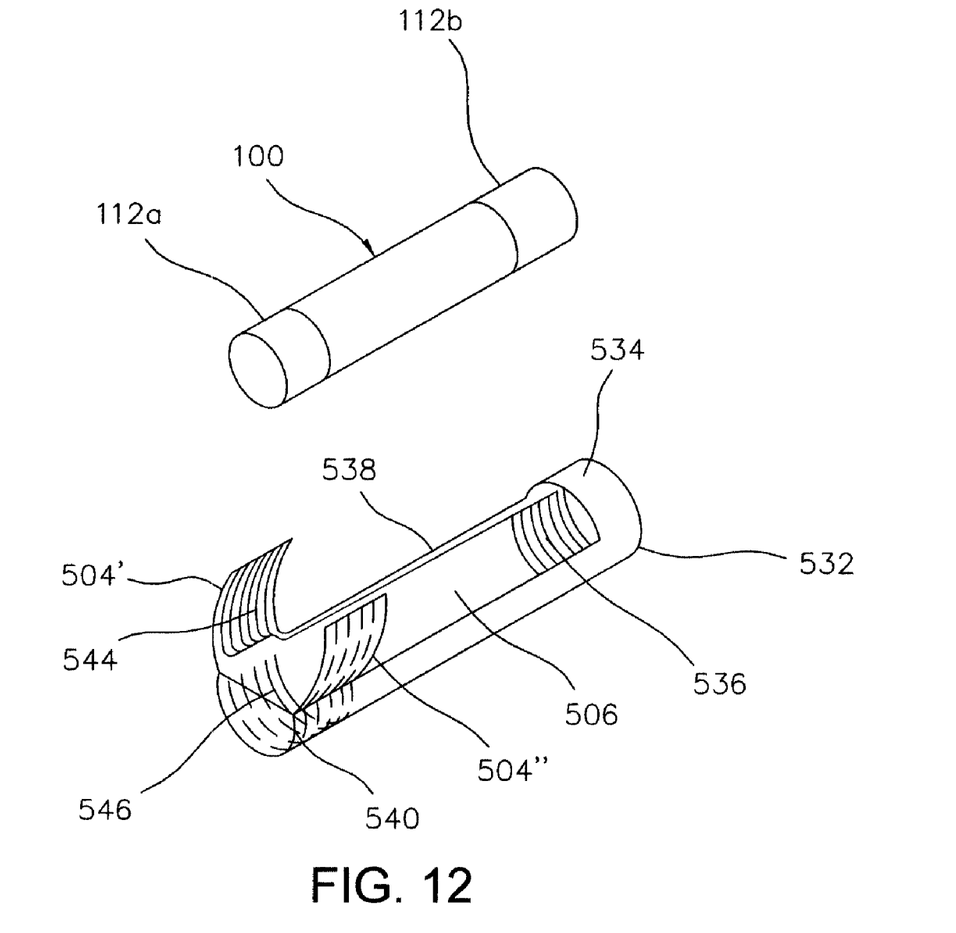
FIG. 12 is a next alternative embodiment of the placement structure of FIG. 3 wherein inner portions of the wings and the cavity include conductive layers (preferably a plurality of conductive paths) to provide additional electrical coupling between the electrodes of the implantable device transversely across the neural/muscular tissue using a pair of wings.

With the implantable device 100 within the cavity 506, the placement structure 500 may be placed in contact, e.g., snapped around, with neural/muscular 512 tissue using the elasticity of the wings 504 to capture/grab the neural/muscular tissue 512 (see FIG. 5, also see the cross sectional view of FIG. 10). As noted in FIGS. 6 and 7, preferred embodiments include structures that rely upon the elasticity of the wings 504 to capture/grab the neural/muscular tissue (see FIG. 6) as well as structures that include hook elements 514 that further supplement the elasticity of the wings 504 for capturing/grabbing the neural/muscular tissue 512.

Figure 8:
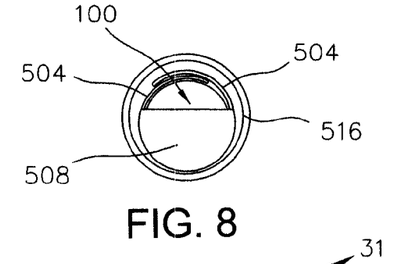
FIG. 8 is an exemplary laparoscopic device suitable for implanting the placement structure of the present invention which in turn is holding one of the aforementioned implantable devices in close proximity to neural/muscular tissue.
Figure 9:
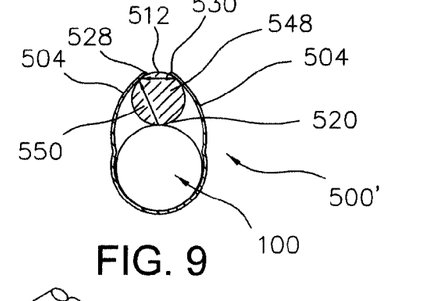
FIG. 9 is a cross sectional view of that shown in FIG. 8 along the line 31-31 where the wings of the placement structure have been folded inward toward the implantable device before insertion, e.g., via its tip, into the hollow portion of the laparoscopic device.

While a cut-down procedure may be used, it is preferred that implantable device 100 within the placement structure 500 be inserted with a hypodermic type insertion tool, e.g., an adapted laparoscopic device 516 (see FIG. 8 and U.S. Pat. No. 6,582,441 which is incorporated herein by reference). In preparation for implantation, the wings 504 of the placement structure 500 are preferably folded inward in proximity to the implantable device 100 within holder 502 and the combination is inserted within the laparoscopic device 516 (see FIG. 9). The laparoscopic device 516 is then inserted as is known in the art into the patient until the tip 518 of laparoscopic device 516 approaches the desired insertion point of the neural/muscular tissue. Upon reaching its desired insertion point, the placement structure 500 is ejected from the laparoscopic device 516 (or conversely and equivalently, the laparoscopic device 516 is withdrawn while the placement structure 500 is held at the desired insertion point) and the wings 504 elastically extend to their nominal position (see FIG. 6) where they are suitable for capturing the neural/muscular tissue 512.

In a first preferred embodiment 500' (see FIG. 5), the electrodes 112 of the implantable device 100 directly make contact with the neural/muscular tissue 512 at electrode/tissue contact points 520 and 522 (for the exemplary two electrode implantable device 100). Accordingly, the initial depolarization (or sensing) associated with the implantable device 100 extends axially along the neural/muscular tissue 512.

In a second preferred embodiment 500'' (see FIG. 11), the wings 504 and a portion of the cavity 506 include conductive layers 524, 526 (preferably comprised of a plurality of discrete conductive paths, e.g., comb shaped, slotted, or formed of serpentine paths, to reduce eddy currents and heat build up associated with the receipt of RF fields during charging). Accordingly (again referring to FIG. 10), the conductive layer 524 now additionally makes contact with contact surfaces 528 and 530 (in addition to contact point 520) and thus there are now three contact point areas associated with each electrode 112 and thus current flow within the neural/muscular tissue 512 may be increased without increasing the compliance voltage since there will now be a lower resistance between the electrodes 112 and the neural/muscular tissue 512.

In a third preferred embodiment 500''' (see FIG. 13), the initial depolarization (or sensing) is applied transversely to the neural/muscular tissue 512 through a single pair of wings 504. In this embodiment, the distal end 532 of the capture device 500''' is a boot type structure 534 that is suitable for capturing distal electrode 112b of the implantable device 100. Within the boot type structure 534, a conductive layer 536 (preferably a plurality of paths, e.g., slotted, to reduce eddy circuits, as previously described) electrically connect the distal electrode 112b of the implantable device 100 along pathway 538 to first proximal wing 504' at the proximal end 540 of the capture device 500'''. Preferably, wing 504' is longer/wider than the proximal electrode 112a so that electrical pathway 538 and its associated conductive layers 536 and 542 do not make contact with the proximal electrode 112a. Conductive layer 546 extends from within the cavity 506 at the proximal end 540 to the inner surface of second proximal wing 504''. Accordingly, once inserted, the distal electrode 112b is electrically coupled to first proximal wing 504' and the proximal electrode 112a is electrically coupled to the second proximal wing 504''. Once the placement structure 500''' is used to capture the neural/muscular tissue 512, stimulation vectors 548 and 550 are applied transversely to the tissue 512 (see FIG. 10). Alternatively, the electrical pathways associated with second proximal wing 504'' may be omitted, in which case only stimulation vector 550 is present. (Note, the polarity of the stimulation vector is only shown for exemplary purposes and may be reversed as needed. Furthermore, the use of the term stimulation vector is equally applicable to describe the vector for sensing a neural/muscular signal, i.e., a sensor or stimulation/sensor vector.)

Figure 13:
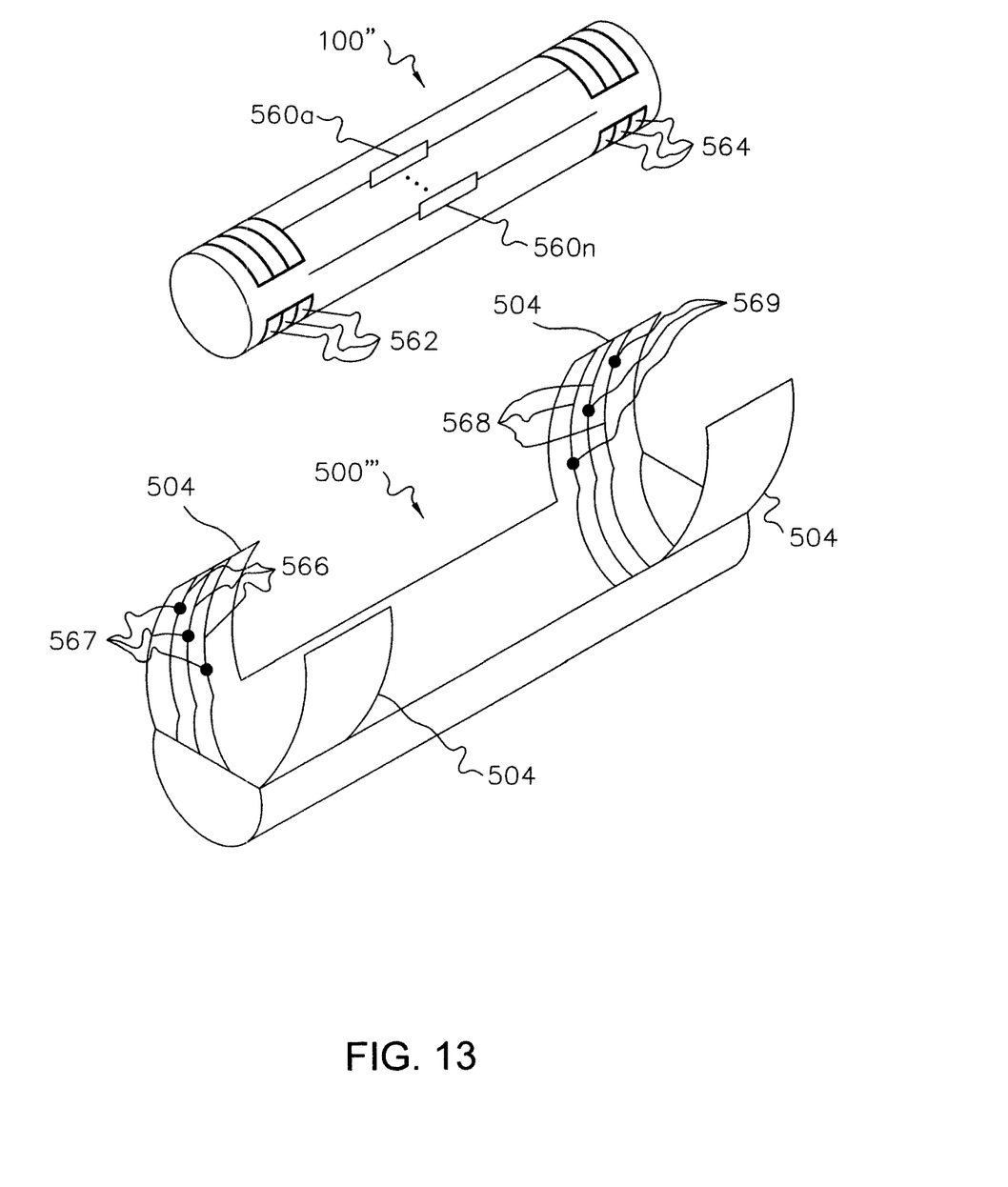
FIG. 13 is an alternative embodiment of the placement structure of FIG. 3 and the implantable medical device of FIGS. 1-2 where the implantable medical device additionally includes a plurality of stimulator/sensor circuitry portions that are coupled via a plurality of electrode connectors and a plurality of conductive paths to inner portions of the wings and the cavity of the placement structure to provide stimulation to or sensing from displaced portions of the neural/muscular tissue.

In the third preferred embodiment 500''', the implantable device 100 is inserted into the capture device 500''' by first inserting the distal end, i.e., electrode 112b, of the implantable device 100 into the boot type structure 534 of the placement structure 500''' and then pressing the proximal end, i.e., electrode 112a, of the implantable device 100 into the proximal end 540 of the placement structure 500'''. This differs from the other two embodiments where both ends of the implantable device 100 are preferably inserted concurrently into the placement structure.

Notably, in the third preferred embodiment, there is only one set of wings, i.e., first and second proximal wings 504' and 504''. Accordingly, during implantation, only a single pair of wings needs to capture the neural/muscular tissue 512 and thus implantation is simplified.

Figure 3:
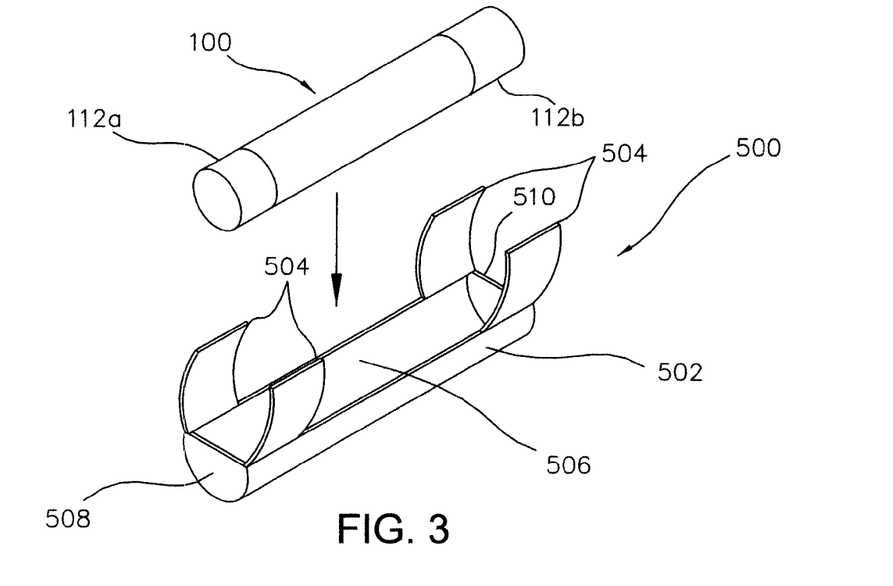
Figure 4:
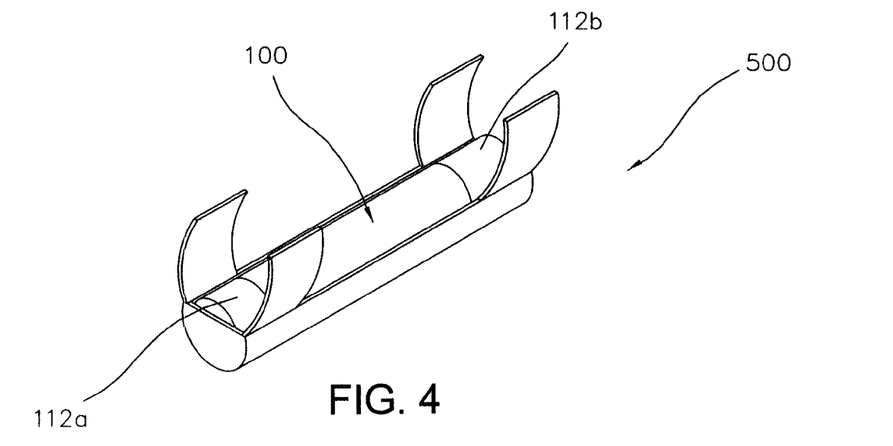
FIG. 4 is a perspective view of the placement structure of FIG. 3 having one of the placement devices held within a hollow cavity within its holder portion.

FIG. 13 is an alternative embodiment 500''' of the placement structure of FIG. 3 and the implantable medical device of FIGS. 1 and 2 wherein the implantable medical device 100'' additionally includes a plurality of stimulator/sensor circuitry portions 560 (e.g., 560a-560n) that are coupled to inner portions of the wings 504 via electrode connectors 562, 564 on the outer surface of the implantable medical device 100'' and the cavity of the placement structure 500''' includes a plurality of conductive paths to provide electrical coupling between the electrode connectors 562, 564 of the implantable medical device 100'' to electrodes 567, 569 within the wings 504 for coupling to displaced portions of the neural/muscular tissue. In this embodiment, the implantable medical device 100'' includes a plurality of stimulator/sensor circuitry portions 560.

To facilitate use of these functions, the implantable medical device 100'' may include a plurality of electrode connectors (preferably semicircular rings) 562, 564 which are coupled to the stimulator/sensor circuitry portions 560. Lower portions of these rings 562, 564 are respectively coupled to the placement structure 500''' when the implantable medical device 100'' is located within the placement structure 500''' to contact electrical pathways 566, 568. Upper portions of these rings/electrodes 562, 564 may make direct contact with the neural/muscular tissue after implantation. These functions may be further facilitated by the placement of electrodes 567, 569 within the wings 504 that have displaced locations within the wings and, in operation, are distributed around the neural/muscular tissue. Preferably, upper portions of the electrical pathways that would otherwise contact the neural/muscular tissue are coated with an insulation layer 570 (not shown) with the exception of the portions corresponding to electrodes 567, 569 to allow the electrodes 567, 569 to perform current steering.

Figure 14:
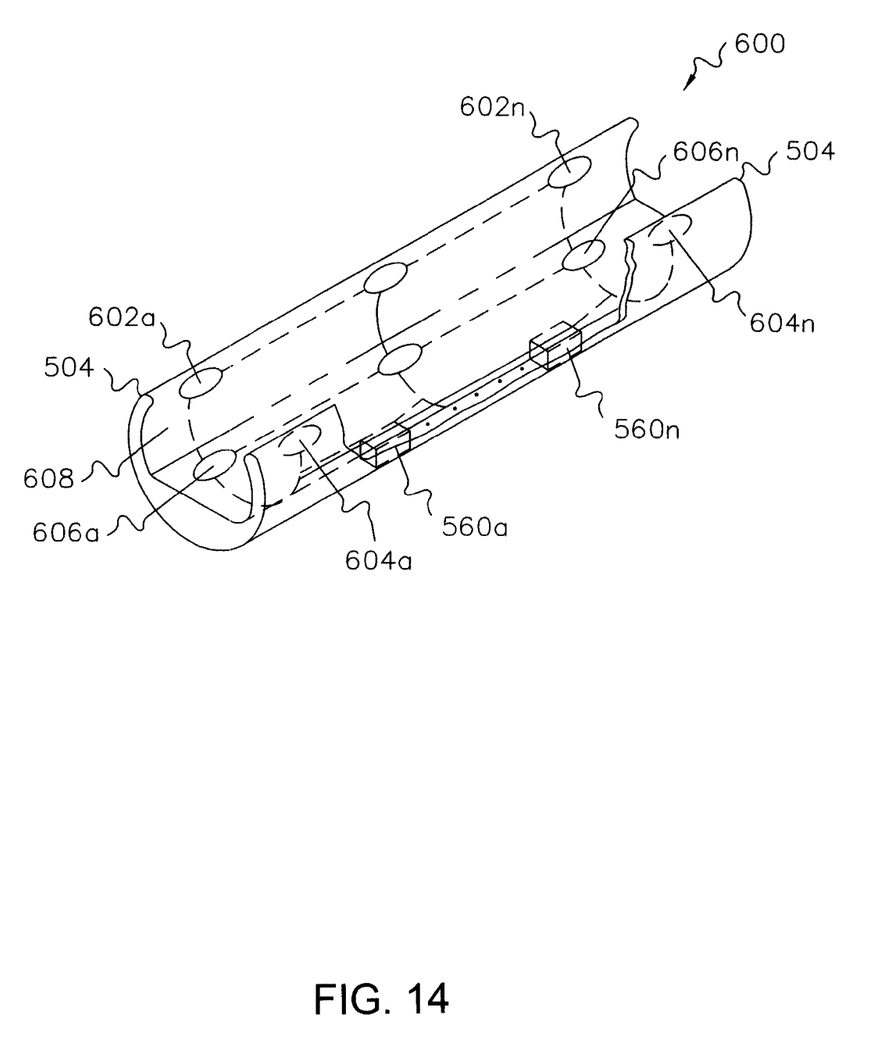
FIG. 14 shows an alternative implementation of that which is functionally described in relation to FIG. 13. However, in this implementation a single, essentially U-shaped, structure having elastic wings is integrally formed which encompasses the functionality of the implantable medical device of FIGS. 1-2 contained within the placement structure.

FIG. 14 shows an alternative implementation of that which was functionally described in relation to FIG. 13. However, in this implementation a single, essentially U-shaped, structure 600 having elastic wings 504 is integrally formed which encompasses the functionality of the implantable medical device 100'' contained within the placement structure 500'''. In this single integral structure 600, a plurality of electrodes 602, 604, 606 (e.g., 602a-602n, 604a-604n, 606a-606n) are distributed (and preferably individually driven by circuitry portions 560 contained within the U-shaped structure 600 along with other circuitry as described in reference to FIG. 3A) within the inner U-shaped cavity 608 of structure 600.

Figure 15:
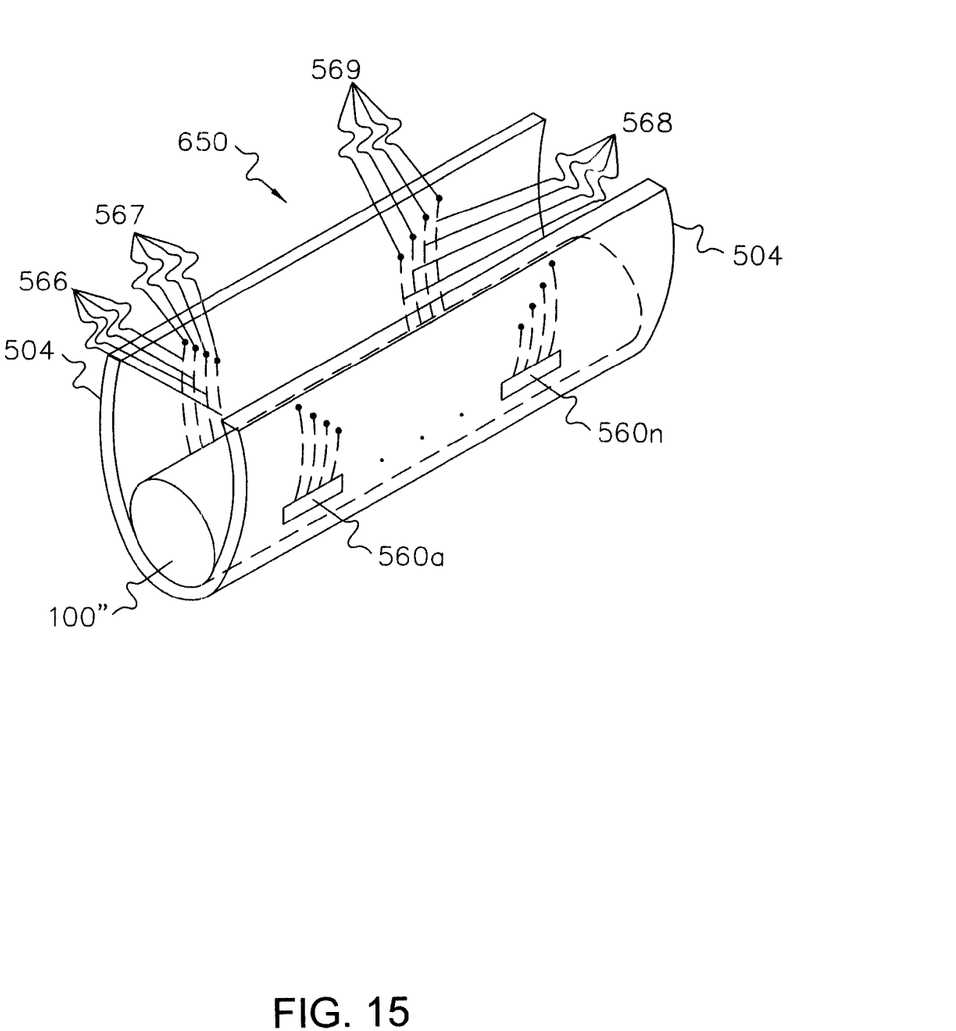
FIG. 15 shows a next alternative implementation of that which is functionally described in relation to FIGS. 13 and 14 to the extent that it too is an integral device but it has its elastic wings 504 formed from a silicone rubber impregnated cloth that is permanently attached to the functional equivalent of the implantable medical device which was described in reference to FIGS. 1-2.

FIG. 15 shows a next alternative implementation of an integral device 650 similar to that shown in FIG. 14 to the extent that it too is an integral device but in this case it has its elastic wings 504 formed from a silicone rubber impregnated cloth that is permanently attached to the functional equivalent of the implantable medical device 100'' described in reference to FIG. 13. In most other aspects, this embodiment is functionally equivalent to that which has been previously described.

While the invention herein disclosed has been described by means of specific embodiments and applications thereof, numerous modifications and variations could be made thereto by those skilled in the art without departing from the scope of the invention. For example, while not expressly shown, the hook portions shown and described in reference to FIG. 7 are equally applicable to the embodiments of FIGS. 14 and 15. It is therefore to be understood that within the scope of the claims, the invention may be practiced otherwise than as specifically described herein.

What is claimed is:

1. A placement structure comprising:
two sets of wings for facilitating placement of an implantable device;
said implantable device having an outer surface and having at least two electrodes, a first electrode and a second electrode configured to be implanted proximate to neural/muscular tissue;
a holder comprised of elastic material that is configured to retain said implantable device and having a hollow longitudinal cavity;
said hollow longitudinal cavity configured to accept said implantable device across its length and perpendicular to the longitudinal axis of the longitudinal cavity;
said hollow longitudinal cavity having a proximal portion and a distal portion configured for holding and retaining said implantable device;
said hollow longitudinal cavity configured to retain said implantable device and said first electrode and said second electrode in direct contact with the neural/muscular tissue;
said implantable device snapped into said hollow longitudinal cavity where it is elastically retained by said elastic material of said holder;
at least two sets of elastic wings comprising a first set and a second set of elastic wings configured to capture neural/muscular tissue; and
said placement structure comprised of biocompatible plastic.

2. The placement structure of claim 1 wherein said biocompatible plastic comprises silicone elastomer.

3. The placement structure of claim 1 wherein said at least one of said at least two sets of elastic wings additionally comprises a hook portion configured to capture the neural/muscular tissue.

4. The placement structure of claim 1: wherein
said at least two sets of elastic wings of said placement structure comprise inner and outer surfaces with said inner surfaces of said at least two sets of elastic wings directed toward said holder; and
wherein said placement structure is configured to retain neural/muscular tissue in contact with said at least two electrodes of said implantable device by providing an elastic force from said inner surfaces of said at least two sets of elastic wings toward said implantable device within said holder.

5. The placement structure of claim 1: wherein
said at least two sets of elastic wings of said placement structure comprise an inner and an outer surface and at least one of said at least two sets of elastic wings includes an electrically conductive portion on said inner surface that provides an electrically conductive path to a portion of said hollow cavity of said holder; and
wherein at least one of said at least two electrodes of said implantable device is electrically connected to said inner surface of at least one of said at least two sets of elastic wings when said implantable device is inserted within said holder.

6. The placement structure of claim 5 wherein said electrically conductive portion is configured to minimize eddy currents.

7. The placement structure of claim 6 wherein said electrically conductive portion comprises a comb shape.

8. The placement structure of claim 6 wherein said electrically conductive portion comprises serpentine paths.

9. The placement structure of claim 5: wherein
said implantable device comprises said at least two electrodes and said placement structure comprises a first set and a second set of elastic wings; and wherein
said first set of elastic wings electrically connects to said first electrode of said implantable device and said second set of elastic wings electrically connects to said second electrode of said implantable device.

10. The placement structure of claim 5: wherein
said implantable device comprises a proximal electrode and a distal electrode;
said placement structure comprises a first opposing wing and a second opposing wing, both having an inner portion;
further comprising a first electrically conductive path between said proximal portion of said hollow cavity and said first opposing wing;
further comprising a second electrically conductive path between said distal portion of said hollow cavity and said second opposing wing, wherein said proximal electrode of said implantable device is electrically connected to said inner portion of said first opposing wing and said distal electrode of said implantable device is in electrical communication with said inner portion of said second opposing wing when said implantable device is inserted within said holder.

11. The placement structure of claim 10: wherein
said distal portion of said holder includes a boot type structure comprising an inner surface for holding the distal end of said implantable device;
wherein at least a portion of said inner surface of said boot type structure includes electrically conductive paths configured to provide electrical communication between said distal electrode of said implantable device and said second wing when said implantable device is inserted in said holder.

12. The placement structure of claim 5: wherein
said implantable device comprises a plurality of sensor/stimulator portions and a plurality of electrode connectors at said outer surface of said implantable device, said plurality of sensor/stimulator portions coupled to said plurality of electrode connectors, said placement structure additionally comprising:
a plurality of electrodes distributed within each of said elastic wings;
a plurality of electrically conductive portions within said holder and said hollow cavity configured to couple said plurality of electrode connectors of said implantable device to said plurality of electrodes in each of said elastic wings; and wherein
said structure is configured to interface to said plurality of electrodes to selectively sense signals from the neural/muscular tissue and/or configured to steer stimulation currents to selective portions of the neural/muscular tissue.

13. An implantable placement structure configured to facilitate placement proximate to neural/muscular tissue of stimulator/sensor device for modifying and/or affecting the neural/muscular tissue, said implantable placement structure comprising:
a biocompatible holder portion forming a hollow U-shaped cavity, and having a longitudinal axis, comprising at least one set of elastic wings further comprising inner surfaces configured to capture neural/muscular tissue;
stimulator/sensor circuitry integrally contained within said biocompatible holder;
said implantable placement structure comprising said hollow U-shaped cavity and configured to receive said stimulator/sensor device across its length and perpendicular to the longitudinal axis of the U-shaped cavity;
at least two electrodes electrically coupled to said stimulator/sensor circuitry integrally contained within said U-shaped cavity;
said implantable placement structure suitable for retaining neural/muscular tissue in direct contact with said at least two electrodes by providing an elastic force from said inner surfaces of said at least one set of elastic wings toward the neural/muscular tissue;
said implantable placement structure comprised of silicone elastomer; and
wherein said at least one set of elastic wings is comprised of a silicone impregnated cloth.

14. The placement structure of claim 13 wherein at least one of said at least one set of elastic wings additionally comprises a hook portion configured to capture the neural/muscular tissue.

* * * * *